United States Patent [19]
Carrell et al.

[11] Patent Number: 5,514,808
[45] Date of Patent: May 7, 1996

[54] HYDROXYL IONS AS UNIQUE THERAPEUTIC AGENTS AND COMPOUNDS THAT MODULATE THESE IONS

[75] Inventors: Delton R. Carrell; Edward J. Cragoe, Jr., both of Nacogdoches, Tex.

[73] Assignee: FHJ Scientific, Inc, Houston, Tex.

[21] Appl. No.: 295,988

[22] Filed: Aug. 25, 1994

Related U.S. Application Data

[63] Continuation-in-part of Ser. No. 134,137, Oct. 8, 1993, abandoned.

[51] Int. Cl.$^6$ .................................................. C07D 213/65
[52] U.S. Cl. ........................ 546/335; 544/335; 544/336; 562/441; 562/442; 562/443; 562/444; 562/451; 562/505; 562/506; 562/507; 562/567; 562/575
[58] Field of Search ................. 546/335; 562/441, 562/442, 443, 444, 451, 505, 506, 507, 567, 575; 544/335, 336

[56] References Cited

U.S. PATENT DOCUMENTS

| | | | |
|---|---|---|---|
| 3,075,924 | 1/1963 | Rubin | 424/319 |
| 3,151,084 | 9/1964 | Schiltz | 424/319 |
| 3,492,238 | 1/1970 | Wohlberg | 424/542 |
| 3,920,020 | 11/1975 | Kraskin | 128/290 |
| 3,932,607 | 1/1976 | Hesselgren | 424/52 |
| 3,935,862 | 2/1976 | Kraskin | 128/282 |
| 3,965,048 | 6/1976 | Murtaugh | 252/527 |
| 3,975,313 | 8/1976 | Shelmire, Jr. | 424/542 |
| 4,107,331 | 8/1978 | Rosenberg | 424/319 |
| 4,337,269 | 6/1982 | Berke et al. | 424/289 |
| 4,528,370 | 7/1985 | Lai | 544/173 |
| 4,584,121 | 4/1986 | Blaschke et al. | 252/106 |
| 4,767,786 | 8/1988 | Farrish | 514/561 |
| 4,847,083 | 7/1989 | Clark | 424/642 |
| 4,868,213 | 9/1989 | Farrish | 514/561 |
| 4,915,864 | 4/1990 | Kita et al. | 252/117 |
| 5,015,409 | 5/1991 | Read, Jr. et al. | 252/108 |

FOREIGN PATENT DOCUMENTS

| | | |
|---|---|---|
| 0106727 | 4/1984 | European Pat. Off. |
| 0339531 | 2/1989 | European Pat. Off. |
| 0629606 | 12/1994 | European Pat. Off. |
| 0045997 | 4/1981 | Japan ............................ 514/561 |

OTHER PUBLICATIONS

Advanced Organic Chemistry, Mar. 1985 3rd Ed, p. 307.
Material Safety Data, Jan. 10, 1990; W. R. Grace & Co., Organic Chemicals Division, 55 Hayden Avenue, Lexington, MA, USA 02173.
Technical Information, Jan. 8, 1976; Hampshire, Organic Chemicals Division, W. R. Grace & Co., 55 Hayden Avenue, Lexington, MA 01273.
Giraud–Clenet et al, C. R. Acad. Sci, Paris, Ser. C., vol. 268, No. 1, pp. 117–20, 1969.
Farfan, Synthesis, vol. 10, pp. 927–929, 1987.
Chemical Abstracts, vol. 120, No. 21, Abstract 271.1006, May 23, 1994, p. 1147 derived from Lu et al, Chin. Chem Letters, 1993, vol. 4, No. 8, pp. 689–692.

*Primary Examiner*—C. Warren Ivy
*Assistant Examiner*—Zinna N. Davis
*Attorney, Agent, or Firm*—Frank J. Uxa

[57] ABSTRACT

The invention concerns the discovery of the surprising and unexpected therapeutic effects of hydroxyl ions. The observed medicinal properties of these ions are both novel and broad in scope. The acute corrosive effects and toxicity of hydroxyl ions on living tissue has previously overwhelmed their therapeutic attributes. Unique hydroxyl ion modulating compounds have been discovered and are within the scope of the invention. When used appropriately as companions with hydroxyl ions, these modulating compounds obviate and attenuate the harmful effects of hydroxyl ions, unmasking and revealing their previously unknown and undemonstratable therapeutic properties. These hydroxyl ion modulating compounds do not significantly interfere with the surprising and unexpected therapeutic benefits of the hydroxyl ions. The novel hydroxyl ion modulating compounds are generally characterized as N,N-disubstituted-aminoacetate salts and substituted N,N-substituted-aminoacetate salts.

10 Claims, No Drawings

HYDROXYL IONS AS UNIQUE THERAPEUTIC AGENTS AND COMPOUNDS THAT MODULATE THESE IONS

RELATED APPLICATIONS

This application is a continuation-in-part of application Ser. No. 08/134,137 filed Oct. 8, 1993, now allowed

BACKGROUND OF THE INVENTION

The present invention relates to the discovery of the novel use of hydroxyl ions in a wide variety of therapeutic applications. This medicinal property of hydroxyl ions has not been observed previously due to their severe toxicity and tissue irritating effects. However, when a unique hydroxyl ion-modulating compound is used as a companion with hydroxyl ions, the harmful effects are attenuated, unmasking their previously unknown novel therapeutic activity. Thus, the invention also relates to the novel compounds that modulate and attenuate the toxic and harmful effects of hydroxyl ions. The invention includes compositions composed of hydroxyl ions and their companion modulating compounds, therapeutic methods of using such compositions and methods of preparing such compositions and their novel components.

Compositions that are applied to human or animal tissue or administered in a variety of other ways to achieve a desired therapeutic effect possess substantially neutral pH values. This is because the irritating and toxic effects of such compositions are directly related to their degree of acidity or alkalinity.

Farrish U.S. Pat. Nos. 4,767,786 and 4,868,213 disclose the use of alkali metal salts of hydroxy alkyl amine-substituted carboxylic acids to disinfect and clean animate objects, surfaces and animal tissue, and to reduce pain and itching. These patents disclose a commercially available product sold by W. R. Grace & Co. under the trademark Hampshire DEG. Since this material is a reaction product of a mixture of sodium cyanide, soda lye, formaldehyde and water, the presence of some of these agents, as well as a variety of major and minor reaction products, is expected. According to the Material Safety Data Sheet published by W. R. Grace & Co., Hampshire DEG contains, among other things, 48–49% by weight of sodium diethanolglycinate (sodium salt of N,N-bis(2-hydroxyethyl)glycine or sodium N,N-bis-(2-hydroxyethyl)aminoacetate), 1–2% by weight of sodium hydroxide and trisodium nitrilotriacetate in an amount of less than 0.5% by weight. Hampshire DEG is also known to contain minor amounts of one or more free amines and has a pH of 13–14.

As noted above, the Material Data Sheet states that Hampshire DEG includes trisodium nitrilotriacetate, which "may reasonably be anticipated to be a carcinogen" according to the Fourth Annual Report on carcinogens (NTP85-022, 1985) page 140. The trisodium nitrilotriacetate is apparently formed during the production of the sodium diethanolglycinate and is not removed during the volatilization process designed to remove amines, as disclosed in the Farrish patents. Other than Hampshire DEG, the Farrish patents do not disclose the combination of hydroxyl ions and alkali metal salts of hydroxy alkyl amine-substituted carboxylic acids, and do not suggest any direct cooperation between hydroxyl ions and such salts or that hydroxyl ions per se have any therapeutic benefits. The Farrish patents disclose that anionic surface active agents are used to reduce irritating effects from high pH, and that the carboxylic acid salts reduce the harmful effects of the anionic surface active agents.

Murtaugh U.S. Pat. No. 3,965,048 discloses drain cleaning compositions including an aqueous solution of a potassium salt of nitrilotriacetic acid, N-2-hydroxyethylimino diacetic acid, an alkylene polyamine polycarboxylic acid, or mixtures thereof and potassium hydroxide, with the composition being free of other alkali metal ions. This patent exemplifies compositions which have large molar excesses of potassium hydroxide. Also, this patent does not disclose any therapeutic or similar applications for such compositions.

Japanese Patent Application 56-45997 discloses an alkaline detergent for hard surfaces containing water, 17–25% by weight of sodium hydroxide and 4–18% by weight of sodium 2-hydroxyethyl imino-diacetate. Thus, these compositions involve large molar excesses of sodium hydroxide. No therapeutic or similar applications of such composition are disclosed.

Kita et al U.S. Pat. No. 4,915,864 discloses an aqueous solution of a strong alkali, a nonionic surface active agent and, as a solubilizing agent, one or more carboxylic acids having the formula:

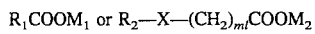

$$R_1COOM_1 \text{ or } R_2\text{—}X\text{—}(CH_2)_{ml}COOM_2$$

in which $R_1$ and $R_2$ each represents a $C_{4-18}$ linear aliphatic hydrocarbon group, $C_{4-18}$ aromatic hydrocarbon group, $M_1$ represents a H, an alkali metal, an aliphatic amine having a $C_{1-4}$ carbon atom content, ammonia, or an alkanolamine, X represents a group selected from $>NH$, $>N(CH_2)_{nl}COOM_2$, or $CHCOOM_2$, $M_2$ represents a H, an alkali metal, an aliphatic amine having a $C_{1-4}$ carbon atom content, ammonia, or an alkanolamine, and ml and nl independently indicate integers of 1–3. Kita et al uses large molar excesses of strong alkali and does not disclose any therapeutic or similar applications for such compositions.

Berke et al U.S. Pat. No. 4,337,269 discloses a product formed by the reaction of glycine, an alkyl substituted glycinate, or salts of these compounds with formaldehyde as a biocidal agent which inhibits microorganism growth. This patent discloses that the composition is prepared by mixing equal molar amounts of glycine and alkali metal hydroxide with formaldehyde. No excess hydroxyl ions are included, and no pharmaceutical compositions or therapeutic applications are disclosed.

Giraud-Clenet et al, C.R. Acad. Sc. Paris, Series C 1969, 268(1), p. 117–120, discloses the preparation of certain N-(beta-hydroxyethyl)-alpha-amino acid intermediates by selective hydroxyethylation. The preparation involves producing 3-(R-substituted)-4-(2-hydroxyethyl)-2-morpholones which are treated with potassium hydroxide to give alpha-[N,N-bis(2-hydroxyethyl)-amino acids that are converted to amides. Only two such acids are disclosed and are used only as chemical intermediates. Further, no combinations of such acids and excess hydroxyl ions are disclosed or suggested. In addition, the methodology used by Geraud-Clenet et al to produce the acids disclosed has only limited applicability and is not effectively useable to produce many acids.

SUMMARY OF THE INVENTION

The present invention involves the discovery of the unique and wide-ranging therapeutic benefits of hydroxyl ions. New compounds, compositions, for example, pharmaceutical compositions, therapeutic methods and production processes have been discovered. Severe tissue irritation, toxicity and damage have heretofore been the normal consequence of exposing animal and human tissues to even modest concentrations of hydroxyl ions, for example, sufficient to provide a pH of above about 8. In total and complete contrast to such detrimental effects of hydroxyl ions, it has unexpectedly and surprisingly been found that hydroxyl ions, even high concentrations of hydroxyl ions, when used in combination with one or more novel hydroxyl ion modulating compounds, as set forth herein, not only do not exhibit the above-noted detrimental effects but actually are very effective in providing a wide range of advantageous therapeutic effects and other benefits. Such advantageous results are achieved at pHs above about 10 or about 12, or even above about 13 or about 14. Thus, the present hydroxyl ion modulating compounds selectively affect or modulate the properties of hydroxyl ions; substantially reducing or eliminating the detrimental effects hydroxyl ions normally have on human and animal tissues, while allowing the unexpected advantageous therapeutic effects and other benefits of hydroxyl ions to be manifest.

Hydroxyl ions, in combination with the present hydroxyl ion modulating compounds, have been found to be highly effective in pharmaceutical and other compositions in providing substantial benefits. For example, the harmful effects of the hydroxyl ions are modulated without substantially interfering with the surprising and unexpected benefits that can be obtained from hydroxyl ion-containing compositions, such as the present compositions, once the harmful effects of the hydroxyl ions have been modulated. The present compounds may, in fact, assist the hydroxyl ions in achieving the benefits, e.g., the desired therapeutic effects and other beneficial results such as in products used for wound healing and in caring for a contact lens, obtained in accordance with the present invention.

The present compositions which include relatively high concentrations of hydroxyl ions unexpectedly provide outstanding and broad-ranging advantageous therapeutic effects and other benefits, while avoiding many of the problems which exist in the prior art. For example, in one embodiment, the compositions are free of carcinogenic material. Further, the present compositions have beneficial component molar ratios which are different from the component molar ratios disclosed by the prior art. The present compositions have been found to provide a wide range of advantageous therapeutic effects, for example, to cure, relieve, manage, heal, treat and/or prevent various conditions, such as ocular conditions, oral conditions, ear, nose and throat conditions, dermal conditions, topical conditions, wound conditions and internal conditions effectively and without undue tissue damage, such as would otherwise be expected from the high concentration of hydroxyl ions present in the composition. Also, the present compositions can be compounded into contact lens care products to be effective in caring for contact lenses.

Methods for providing a desired therapeutic effect and for caring for a contact lens using the present compositions are included in the scope of the present invention.

Further, processes for producing the present compounds and compositions are included within the scope of the present invention.

In one broad aspect, the present invention is directed to novel hydroxyl ion modulating compounds having the formula

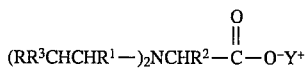

wherein each R is independently selected from the group consisting of H, alkyl having 1 to 4 carbon atoms, phenyl and hydroxyalkyl having 1 to 4 carbon atoms; each $R^1$ is independently selected from the group consisting of H, alkyl having 1 to 3 carbon atoms and hydroxyalkyl having 1 to 3 carbon atoms; $R^2$ is selected from the group consisting of alkyl having 1 to 5 carbon atoms, hydroxyalkyl having 1 to 5 carbon atoms, phenyl, phenylalkyl, heterocyclic, heterocyclicalkyl, cycloalkyl having 3 to 6 carbon atoms, substituted alkyl and H, provided that when $R^2$ is H, n-alkyl, $CH_2OH$ or phenylalkyl, one or both $RR^3CHCHR^1$— groups are not $CH_2OHCH_2$— or $CH_3CHOHCH_2$—; each $R^3$ is independently selected from the group consisting of H, alkyl, hydroxyalkyl, hydroxy and phenyl; and $Y^+$ is selected from the group consisting of $Na^+$, $K^+$, $Li^+$, $(CH_3)_4N^+$ $(C_2H_5)_4N^+$, $C_6H_5$, $(CH_3)_3N^+$, and guanidinium. Since each R, $R^1$ and $R^3$ is selected independently of the other R, $R^1$ and $R^3$, respectively, each $RR^3CHCHR^1$— group can be the same or different. Such compounds have been found to have the ability to modulate one or more of the detrimental effects of hydroxyl ions, without unduly diminishing at least one beneficial effect of such hydroxyl ions. In addition, such compounds, or mixtures of such compounds, can be effective in assisting, when used in combination with hydroxyl ions, in achieving certain desired therapeutic effects and other benefits.

In another broad aspect of the present invention, pharmaceutical compositions useful in providing at least one desired therapeutic effect when administered to a human or an animal are provided. Such compositions comprise a therapeutically effective amount of a hydroxyl ion component; and an effective amount of a hydroxyl ion modulating component. The hydroxyl ion modulating component is selected from N,N-disubstituted-aminoacetate salts, substituted N,N-disubstituted-aminoacetate salts and mixtures thereof. The hydroxyl ion modulating component is present in the compositions in a molar concentration greater than the molar concentration of the hydroxyl ion component. In one embodiment, the present compositions are such that the hydroxyl ion modulating component is preferably other than sodium diethanolglycinate and/or are preferably free of byproducts and impurities, such as amines, carcinogenic material, namely trisodium nitrilotriacetate, and the like, produced or present during the formation of the hydroxyl ion modulating component, for example, sodium diethanolglycinate. The molar ratio of hydroxyl ion modulating component to hydroxyl ion component in the compositions can be greater than 1 and less than 5.2, or can be greater than 10.5. These features clearly distinguish the present compositions from compositions derived from Hampshire DEG disclosed in the above-noted Farrish patents.

In one embodiment, the present pharmaceutical compositions are ophthalmically acceptable and are useful in providing a desired therapeutic effect to a mammalian eye when administered thereto.

Ophthalmically acceptable compositions which include a hydroxyl ion component and an effective amount of a hydroxyl ion modulating component are useful in products for caring for contact lenses. The hydroxyl ion component is present in such compositions in an amount which alone or in combination with the hydroxyl ion modulating component is effective in providing one benefit to a contact lens which is contacted with the composition. The hydroxyl ion modulating component is present in a molar concentration greater than the molar concentration of the hydroxyl ion component.

In another broad aspect of the present invention, methods for providing desired therapeutic effects to a human or an animal are provided. Such methods comprise administering to a human or an animal in need of the desired therapeutic effect an amount of one of the pharmaceutical compositions described herein. Such amount of pharmaceutical composition is effective in providing the desired therapeutic effect to a human or an animal. Among the desired therapeutic effects that can be obtained using the present pharmaceutical compositions are ocular therapeutic effects, oral therapeutic effects, ear, nose and throat therapeutic effects, dermal therapeutic effects, topical therapeutic effects, wound therapeutic effects, and internal therapeutic effects. Of course, more than one desired therapeutic effect, even more than one different type of therapeutic effect, can be obtained by a single administration of the present pharmaceutical compositions to the human or animal. In one particularly useful embodiment, the desired therapeutic effect includes at least one of the management of a wound, the healing of a wound and the reduction of pain from a wound. The present compositions possess outstanding and remarkable wound healing properties including, but not limited to, the control of microbial action, edema, erythema and pain, and also act to enhance or improve the quality of scar tissue, for example, relative to scar tissue from an identical wound not treated with such compositions.

Methods for providing a desired therapeutic effect to a mammalian eye are also included. Such methods comprise administering to a mammalian eye an amount of the ophthalmically acceptable pharmaceutical compositions described herein effective in providing the desired therapeutic effect to the mammalian eye.

In addition, methods for caring for a contact lens are provided and comprise contacting a contact lens with an effective amount of the ophthalmically acceptable compositions described herein at conditions effective in imparting at least one benefit to the contact lens. Among the benefits imparted to a contact lens using the present compositions are disinfecting the contact lens, cleaning the contact lens and enhancing the wearability of the contact lens.

Processes for the preparation of compositions comprising a hydroxyl ion modulating component are also within the scope of the present invention. Such hydroxyl ion modulating component is selected from the group of compounds having the formula

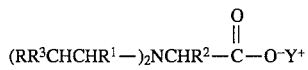

and mixtures thereof, wherein each R is independently selected from the group consisting of H, alkyl, hydroxyalkyl, cycloalkyl, aryl and substituted counterparts thereof; each $R^1$ is independently selected from the group consisting of H, alkyl, hydroxyalkyl and substituted counterparts thereof; each $R^2$ is independently selected from the group consisting of H, alkyl, cycloalkyl, aryl, aralkyl, heterocyclic, heterocyclicalkyl and substituted counterparts thereof; each $R^3$ is independently selected from the group consisting of H, alkyl, hydroxyalkyl, hydroxy, aryl and substituted counterparts thereof; and $Y^+$ is selected from the group consisting of $Na^+$, $K^+$, $Li^+$, $(CH_3)_4N^+$, $(C_2H_5)_4N^+$, $(CH_3CH_2CH_2CH_2)_4N^+$, $C_6H_5(CH_3)_3N^+$, and guanidinium. Such processes comprise contacting a compound having the formula

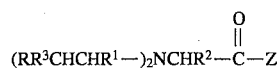

wherein Z is selected from the group consisting of COOH and $COOR_4$ ($R^4$ being selected from the group consisting of alkyl), —CN, —$CONH_2$, —CONH(alkyl), —CON(alkyl)$_2$, —C(=NH)NH$_2$ and —CONHNH$_2$, with sufficient YOH, preferably with at least about 1.1 to about 1.35 molar equivalents of YOH, at effective reaction conditions to react the compound and YOH and form a reaction product. When Z is other than COOH, the compound is treated with YOH at aqueous hydrolysis conditions. The reaction product is preferably concentrated and/or purified, for example, is subjected to lyophilization conditions, to produce a product. This product, in turn, is preferably converted in a solution with pyrogen-free water so that the solution contains about 0.1% to about 20% by weight of the product. The product produced by the present processes includes the hydroxyl ion modulating component and is preferably combined with sufficient hydroxyl ion component, for example, the YOH used in the above-noted treatment step, to yield a formulation having a molar ratio of hydroxyl ion modulating component to hydroxyl ion component as described herein with regard to the present compositions, preferably in the range of about 3 to about 9.

DETAILED DESCRIPTION OF THE INVENTION

Hydroxyl ions have been discovered to possess a wide variety of surprising therapeutic effects.

Certain compounds and mixtures of such compounds have been found to have the outstanding and unexpected property of modulating or attenuating one or more of the harmful effects of hydroxyl ions, preferably without substantially interfering with the surprising and unexpected benefits that have been found obtainable from hydroxyl ion component—containing compositions, such as the present compositions, once the harmful effects of the hydroxyl ion component, in particular the hydroxyl ions, have been modulated. In addition, the present compounds and mixtures thereof can assist, when used in combination with hydroxyl ions, in achieving benefits, for example, desired therapeutic effects and other beneficial results.

The present compounds are generally described as N,N-disubstituted-aminoacetate salts, substituted N,N-disubstituted-aminoacetate salts and mixtures thereof. A useful group of compounds are those having the formula:

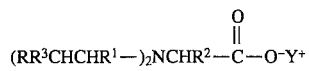

wherein each R is independently selected from the group consisting of H, alkyl, hydroxyalkyl, cycloalkyl, aryl and substituted counterparts thereof; each $R^1$ is independently selected from the group consisting of H, alkyl, hydroxyalkyl and substituted counterparts thereof; $R^2$ is selected from the group consisting of H, alkyl, cycloalkyl, aryl, aralkyl, heterocyclic, heterocyclicalkyl and substituted counterparts thereof; each $R^3$ is independently selected from the group consisting of H, alkyl, hydroxyalkyl, hydroxy, aryl and substituted counterparts thereof and $Y^+$ is selected from the group consisting of $Na^+$, $K^+$, $Li^+$, $(CH_3)_4N^+$, $(C_2H_5)_4N^+$, $(CH_3CH_2CH_2CH_2)_4N^+$, $C_6H_5(CH_3)_3N+$, and guanidinium; and mixtures thereof. Preferably one R group is H.

A preferred group of such compounds are those having the formula

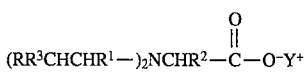

$$(RR^3CHCHR^1-)_2NCHR^2-\overset{\overset{O}{\|}}{C}-O^-Y^+ \quad 5$$

wherein each R is independently selected from the group consisting of H, alkyl having 1 to 4 carbon atoms, hydroxyalkyl having 1 to 4 carbon atoms, cycloalkyl, phenyl and substituted counterparts thereof, more preferably from H, $CH_3$, $CH_2OH$, and $C_6H_5$, and still more preferably from $CH_3$, $CH_2OH$ and $C_6H_5$; each $R^1$ is independently selected from the group consisting of H, alkyl having 1 to 3 carbon atoms, hydroxyalkyl having 1 to 3 carbon atoms and substituted counterparts thereof; more preferably from H, $CH_3$, $CH_2OH$ and $C_2H_5$, still more preferably from H, $CH_3$ and $CH_2OH$; $R^2$ is selected from the group consisting of H, alkyl having 1 to 5 carbon atoms, hydroxyalkyl having 1 to 5 carbon atoms, cycloalkyl having 3 to 6 carbon atoms, aryl, more preferably phenyl, aralkyl, more preferably phenylalkyl, heterocyclic, heterocyclicalkyl and substituted counterparts thereof; each $R^3$ is independently selected from the group consisting of H, alkyl having 1 to 3 carbon atoms, hydroxyalkyl having 1 to 3 carbon atoms, hydroxy, aryl, more preferably phenyl, and substituted counterparts thereof, more preferably from H, OH, $CH_3$ and $C_2H_5$, and still more preferably from H and OH; and $Y^+$ is selected from the group consisting of $Na^+$, $K^+$, $Li^+$, $(CH_3)_4N^+$, $(C_2H_5)_4N^+$, $(CH_3CH_2CH_2CH_2)_4N^+$, $C_6H_5(CH_3)_3N^+$, and guanidinium; and mixtures thereof. Preferably, at least one R is hydroxyalkyl or at least one $R^3$ is hydroxy or hydroxyalkyl. More preferably, each R is independently selected from hydroxy and hydroxymethyl. In one embodiment R or $R^1$ is hydroxymethyl and/or each $R^3$ is hydroxy. When $R_2$ is H, n-alkyl, $CH_2OH$ or phenylalkyl, one or both $RR^3CHCHR^1-$ groups are preferably other than $CH_2OHCH_2-$ or $CH_2CHOHCH_2-$.

Alkyl is any saturated non-aromatic hydrocarbon radical. Examples of the alkyl groups from which certain of the above-noted substituents can be chosen include, but are not limited to, such groups having 1 to about 5 or more carbon atoms, such as methyl, ethyl, propyl, isopropyl, butyl, isobutyl, t-butyl and the like. Examples of the hydroxyalkyl groups from which certain of the above-noted substituents can be chosen include, but are not limited to, such groups having 1 to about 5 or more carbon atoms, such as the alkyl groups noted above substituted with one or more, preferably only one, hydroxy group. The hydroxy group or groups can be located at any point or points on the alkyl chain except the alpha carbon atom, for example, on the beta or gamma carbon atom of the alkyl chain. Examples of cycloalkyl groups from which certain of the above-noted substituents can be chosen include, but are not limited to, such groups having about 3 to about 7 or more carbon atoms, such as cyclopropyl, cyclobutyl, cyclopentyl, cyclohexyl and the like.

Aryl is any hydrocarbon radical having an available bonding cite on an aromatic hydrocarbon ring. Examples of the aryl groups from which certain of the above-noted substituents can be chosen include, but are not limited to, such groups having 6 to about 9 or more carbon atoms, such as phenyl, indenyl, condensed aromatic compounds and the like. Examples of the aralkyl groups for which certain of the above-noted substituents can be chosen include, but are not limited to, such groups having 7 to about 12 or more carbon atoms, such as phenylmethyl, phenylethyl, phenylbutyl, phenylhexyl and the like.

Heterocyclic is any radical including a ring having at least one carbon atom and at least one heteroatom (an atom other than a carbon atom), such as N, S, O and the like. Examples of the heterocyclic groups from which certain of the above-noted substituents can be chosen include, but are not limited to, such groups having about 4 to about 8 or more carbon atoms, such as

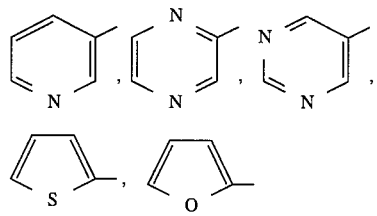

and the like. Examples of the heterocyclicalkyl groups from which certain of the above-noted substituents can be chosen include, but are not limited to, such groups having about 5 to about 10 or more carbon atoms, such as

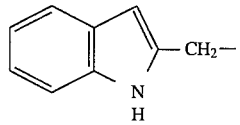

and the like.

The term "substituted counterpart thereof" as it relates to any of the above-noted substituents (other than H) refers to such substituent in which one or more hydrogen atoms are replaced by one or more other species including, but not limited to, monovalent hydrocarbon groups, such as alkyl, alkenyl and alkynyl (such as ethenyl, propenyl, butenyl, ethynyl and the like unsaturated hydrocarbon groups having 2 to about 6 or more carbon atoms) and aryl; heterocyclic groups; halo such as F, Cl, Br and I; $NH_2$; $NO_2$; alkoxy; alkylthio; aryloxy; arylthio; alkanoyl; alkanoyloxy; aroyl; aroyloxy; acetyl; carbamoyl; alkylamino; dialkylamino; arylamino; alkylarylamino; diarylamino; alkanoylamino; alkylsulfinyl; alkylsulfenyl; alkylsulfonyl; alkylsulfonylamido; azo; benzyl; carboxy; cyano; guanyl; guanidino; imino; phosphinyl; silyl; thioxo; ureido or vinylidene or where one or more carbon atoms are replaced by one or more other species including, but not limited to, N, O or S.

In a particularly useful embodiment, each $R^2$ is independently selected from H, $CH_3$, $C_2H_5$, $H_2NC(=NH)$ $-NH(CH_2)_3-$, $NH_2COCH_2-$, cyclopentyl, $HOOCCH_2-$, $HOOCCH_2CH_2-$, $H_2NCOCH_2CH_2-$,

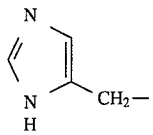

$CH_3CH_2CH(OH)CH_2CH_2-$, $CH_3CH_2CH(CH_3)-$, $(CH_3)CHCH_2-$, $NH_2(CH_2)_4-$, $CH_3SCH_2CH_2-$,

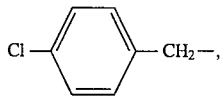

$C_6H_5$—, $C_6H_5CH_2$— $CH_3CH(OH)$—,

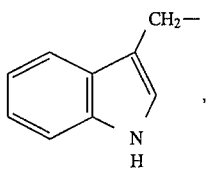

$(CH_3)_2CH$—, $(CH_3)_3C$—, $CF_3$—,

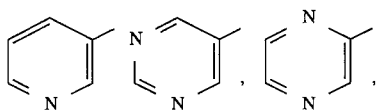

$CF_3CF_2$—, $(CH_2OH)_3C$—,

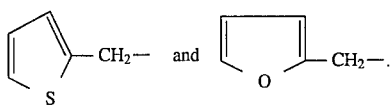

When all of the R, $R^1$, $R^2$ and $R^3$ groups are H, the above-noted compounds are not chiral. However, when only one R is not H, the compounds are chiral; therefore, the compounds represent a racemate or either of two enantiomers. If any two, three or all four of the R, $R^1$, $R^2$ and $R^3$ groups are not H, then the above-noted compounds represent any one of two or more diasteriomers or meso forms, and any of the component racemates and enantiomers. This invention includes each of the possible isomers, steroisomers, tautomers and mixtures thereof of the above-noted compounds.

One type of preferred compounds are those derived from natural amino acids, i.e., those in which the >$CHR^2COO$— moiety is derived from a natural amino acid. In most instances, these compounds belong to the L-series of amino acids.

Specific examples of hydroxyl ion modulating compounds include sodium salts, potassium salts, tetramethylammonium salts, tetraethylammonium salts, benzyltrimethylammonium salts and guanidinium salts and mixtures thereof. Such salts are derived from acids selected from N,N-bis-(2,3-dihydroxypropyl) aminoacetic acid, N,N-bis-(1-hydroxy-2-propyl) aminoacetic acid, N,N-bis-(2-hydroxy-2-phenylethyl) aminoacetic acid, N,N-bis-(1,3-dihydroxy-2-propyl) aminoacetic acid, 2-[N,N-bis-(2,3-dihydroxypropyl) amino] isovaleric acid, 2-[N,N-bis-(2-hydroxyethyl)amino]succinamic acid, 2-[N,N-bis-(2-hydroxyethyl)amino]-3-phenylpropanoic acid, 2-[N,N-bis-(2-hydroxyethyl)amino]isovaleric acid, 2[N,N-bis-(2-hydroxyethyl)amino]-(3-pyridyl)acetic acid, 2-[N,N-bis-(2-hydroxyethyl)amino]-3,3,3-trifluoropropanoic acid, [N,N-bis-(2-hydroxyethyl)amino]phenylacetic acid, N,N-bis-(3-hydroxypropyl)aminoacetic acid, N-(2-hydroxyethyl-N-(2-hydroxypropyl)aminoacetic acid and N-2-hydroxyethyl)-N-(3-hydroxypropyl)aminoacetic acid.

This invention further comprises therapeutic combinations or compositions of the hydroxyl ion modulating component, as described herein, and a hydroxyl ion component. The hydroxyl ion component concentration can be obtained by combining excess base (YOH) with the substituted or unsubstituted N,N-aminoacetate salt or salts. A wide range of hydroxyl ion component concentrations are uniquely therapeutically effective. In order to obtain an effective hydroxyl ion modulating effect, the molar concentration of the hydroxyl ion modulating component in the present compositions is greater than the molar concentration of the hydroxyl ion component. In one embodiment, the molar ratio of the hydroxyl ion modulating component (or HIMC) to the hydroxyl ion component (or HIC) is greater than 1 and less than 5.2, or greater than 10.5. More preferably, the molar ratio of HIMC to HIC in the present compositions is about 3 to about 9. When used in aqueous solutions, the preferred molar concentration range for the HIMC is in the range of about 0.01 to about 2.2.

The innovative compositions of this invention may be prepared as solutions, powders, mouth washes, ointments, creams, gels and other convenient pharmaceutical forms. Effective amounts of appropriate, for example, conventional and well known, ingredients, such as carriers and the like, may be included in order to provide the desired form of the present compositions.

Although the present compositions may be stored for use and/or administered in a solid, e.g. powder, or other form, in use these compositions are combined with a medium effective to ionize the hydroxyl ion component to form hydroxyl ions. In many instances, this ionizing medium is aqueous-based. For example, if the composition is administered as a powder to the skin of a human or animal, moisture on the skin (for example, perspiration or even blood on the skin) can act as the ionizing medium to form an effective amount of hydroxyl ions which are effectively modulated by the hydroxyl ion modulating component, which preferably is also ionized by the ionizing medium. In a particularly useful embodiment, the present compositions include an effective amount, for example, at least about 20% or at least about 50% by weight, of an ionizing medium, more preferably an aqueous-based ionizing medium, such as pyrogen-free water. Including the ionizing medium in the present compositions effectively controls the effective concentration of hydroxyl ions in such compositions and, in certain instances, increases the convenience of administering the compositions to humans or animals.

The compositions of the present invention preferably contain about 0.05% to about 20% by weight of active ingredients, for example, HIMC and HIC. The compositions may also be concentrated, for example, by lyophilization or vacuum volatilization of a portion of the solvent, as desired for other purposes.

One or more other ingredients may be added to the compositions, as desired, including, but not limited to, dyes, pigments, perfumes, etc., for example, up to a total of about 10% by weight. Also, for application to human or animal tissue, the compositions may contain constituents normally present in preparations for this purpose, such as emulsifiers, fatty substances, plant extracts, preservatives, tonicity adjusters and solvents in the customary, effective amounts. The compositions of the present invention may contain any constituent which is not unduly irritating to human or animal tissue either alone or in combination with the active ingredients, and does not significantly affect the pH of the composition. The present compositions are preferably free of anionic surface active agents.

The present invention includes methods for providing one or more desired therapeutic effects to a human or an animal. Such methods comprise administering to a human or animal in need of the desired therapeutic effect or effects an amount of the present pharmaceutical compositions effective in providing the desired therapeutic effect or effects to the human or animal. Such desired therapeutic effects can result or be embodied in or lead to the mitigation, for example, the curing, relieving, managing, healing, treating and/or preventing, of various conditions. Among the desired therapeutic effects that can be obtained using the present compositions are ocular therapeutic effects, oral therapeutic effects, ear, nose and throat therapeutic effects, dermal therapeutic effects, topical therapeutic effects, wound therapeutic effects (that is therapeutic effects to wounds, in particular wound healing effects) and internal therapeutic effects.

Among the ocular therapeutic effects that can be obtained using the present compositions are: ocular wound healing effects; ocular disinfecting effects; ocular analgesic effects and ocular antiseptic effects. The present ocular therapeutic effects are preferably obtained by administering to a mammalian eye or eyes an amount of the present therapeutic composition effective in providing the desired therapeutic effect to the mammalian eye or eyes.

Compositions which include effective amounts of both HIMC and HIC have various applications in contact lens care. For example, such compositions are useful in providing cleaning and/or disinfecting of contact lenses, in reducing contact lens-caused ocular irritation and in increasing contact lens wear comfort. When used in contact lens care applications, such compositions are contacted with the contact lens to be cared for at conditions effective to obtain the desired contact lens treatment or beneficial effect or effects. The present contact lens care compositions may include effective amounts of one or more additional components, for example, tonicity adjusters, wearability components, surfactants, viscosity enhancing components and the like which are conventionally used in contact lens care products.

When used to provide ocular therapeutic effects or to care for contact lenses, the present compositions preferably are ophthalmically acceptable. The term "ophthalmically acceptable" refers to the property of a composition whereby no significant long term detrimental effect results if an effective amount of the composition is administered to the eye or eyes of a human or animal, in particular to the eye or eyes of a mammal. One would expect that the present compositions with relatively large hydroxyl ion concentrations would cause irritation, or even damage, to the mammalian eye, which is one of the most sensitive body organs. Thus, it is indeed surprising and unexpected that the present hydroxyl ion-containing compositions are effective in providing ocular therapeutic effects and in caring for contact lenses, and are, at the same time, ophthalmically acceptable.

Among the oral therapeutic effects that can be obtained using the present compositions include the treatment and/or management of gingivitis, plaque removal and prevention, healing of oral wounds, for example, from dental and surgical procedures, treatment and/or management of cold and other mouth sores. The present composition can also be used to deodorize the mouth, and to provide oral antiseptic effects and oral analgesic effects.

Among the ear, nose and throat therapeutic effects that can be provided using the present compositions are the reduction and elimination of ear infections and ear pain; the treatment and/or management of swimmer's ear; as an ear, nose and throat antiseptic; as a nasal spray to provide decongestion; and as a treatment and/or management agent for sore throat.

Among the dermal therapeutic effects that can be obtained using the present compositions are healing of dermal wounds, meaning to include, but not limited to, burn healing, and the treatment and/or management of acne, sunburn, diaper rash, jock itch and boils. Also, the present compositions can be used to treat contact dermatitis, for example, insect bites/stings, poison ivy/oak and the like; hemorrhoids; vaginal infections, for example, yeast infections; fungal and bacterial infections, for example, athlete's foot, ringworm and the like; cuts and abrasions, for example, to provide antimicrobial, antiedema and antierythemia advantages, as well as relief of pain, improvement of the quality of scar tissue and the like; psoriasis; inflammation; decubitus ulcers; pain; eczema; dermatitis; scabies; shingles; hot spots, for example, on animals such as dogs and the like; and mange in animals. The present compositions can also be used as deodorants.

Among the internal therapeutic effects which can be obtained using the present compositions are wound healing, including, but not limited to, post-surgical wound healing; wound cleaning and disinfecting; analgesic effects; antimicrobial effects; pain reduction and the like.

One primary therapeutic use for the compositions of this invention is for wound healing. The advantage of this therapy is that a contribution is made to more than one, even many, facets of wound healing. Such facets include, but are not limited to, one or more of the following: antimicrobial effects; reduction of local edema and erythema; abatement of pain; increase in the rate of healing; and improvement in scar tissue quality. The wounds can involve one or more of a variety of tissue lesions including cuts, abrasions, surgical lesions, burns, sunburn, etc. The wounds can be caused by accidents or by disease processes such as acne, bed sores, boils, skin and mouth ulcers, gingivitis, etc. The application of the described therapy can be to human or veterinary medical problems.

The therapy can be applied to the skin, mouth, eye, ear or vagina. It can be used as a treatment of an existing medical problem or used prophylactically to prevent lesions, wounds or their sequelae. Examples of the prophylactic use of the compositions of this invention include a solution for the treatment of contact lenses and prevention of dental plaque to avert dental caries and gingivitis. Skin treatment prior to surgery is also included.

The present hydroxyl ion modulating substituted and unsubstituted aminoacetate salts can be prepared by a number of methods. One convenient method comprises the interaction of an appropriate aminoacetic acid shown below with an appropriate base (YOH) under conditions effective in neutralizing the acid and forming the corresponding salt.

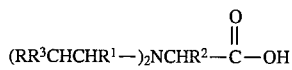

This method is especially useful since, when various combinations or compositions including the present modulating aminoacetate salts and hydroxyl ion components are desired, excess YOH can be included.

The synthesis of compounds of the type represented by Formula (C) (below) can be carried out by a variety of synthetic schemes of which the following is an example.

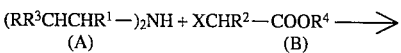

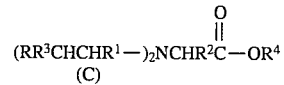

The reaction of an amine of Formula A with a 2-haloalkanoic acid ester of Formula (B) yields an ester of formula (C). Hydrolysis of this ester by any one of several methods yields the corresponding hydroxyl ion modulating compound of the present invention. In this series of reactions, R, $R^1$, $R^2$ and $R^3$ are as described above, X is a halo group, such as chloro, bromo or iodo, and $R^4$ is lower alkyl, such as methyl or ethyl, The 2-haloalkanoic acid esters of formula (B) can be produced by any suitable method, many of which are conventional and well known in the art. These esters are very effective intermediates to the present hydroxyl ion modulating components in which $R^2$ is heterocyclic and heterocyclicalkyl, such as those groups including at least one hetero atom selected from N, S and O The reaction of compounds of Formulas (A) and (B) can be conducted neat or with solvents, such as, an alkanol, for example, ethanol, 2-propanol or 1-propanol; acetonitrile, dimethylformamide, etc. The reaction mixture is conveniently stirred and heated, for example, to temperatures in the range of about 40° C. to the boiling point of the solvent, for a period of about 30 minutes to about 12 hours.

Hydrolysis of a compound of formula (C) can be conducted either under acidic or basic conditions. In either instance, it is conveniently conducted in a water soluble solvent containing water and the solvent, such as methanol, ethanol, 1-propanol or 2-propanol, etc. The solution is conveniently stirred and heated to a temperature in the range of about 40° C. to the boiling point of the solvent mixture for a period of about 30 minutes to about 8 hours. If basic hydrolysis is carried out, a molar excess of a base, such as sodium hydroxide, potassium hydroxide and the like, can be conveniently employed. This produces a salt which is carefully acidified, for example, with hydrochloric acid, sulfuric acid and the like, to produce the modulating compound of the present invention. The product may precipitate from the solution and be isolated by filtration or by chromotography, or the reaction mixture may be evaporated in vacuo and the modulating compound extracted using an organic solvent, water or a mixture of water and an organic solvent. The modulating compound can be isolated from a solvent by evaporation in vacuo. Other methods of producing the modulating compounds include, starting with $$(RR^3CHCHR^1-)_2NCHR^2-Z$$

employing the following reactions:

1. Pyrolysis of tert-butyl esters, i.e., where $$Z=COOC(CH_3)_3.$$

2. Hydrolysis of nitriles, i.e., where Z=—CN.
3. Hydrolysis of anhydrides, i.e., where Z=

$$(RR^3CHCHR^1-)_2NCHR^2-\overset{O}{\underset{\|}{C}}-O-\overset{O}{\underset{\|}{C}}-$$

4. Hydrolysis of acid halides, i.e., where Z=halo.
5. Hydrolysis of amides and related compounds, i.e., where Z=—CONH$_2$, —CONH(alkyl), —CONH(alkyl)$_2$, —CONHNH$_2$, etc.).
6. Oxidation of aldehydes, i.e., where Z=—CHO.
7. Hydrolysis of amidines, i.e., where Z=C(=NH)NH$_2$).

The present invention is illustrated by the following non-limiting examples wherein all parts and percentages are by weight unless otherwise defined.

Since most of the uses of the compositions of this invention are for application topically to a tissue, they can be applied as powders, ointments, or solutions. The solutions can be conveniently applied as sprays and the solids as aerosols. The concentration of the active ingredient may be in the range of about 0.1% to about 20% depending on the specific preparations and the number of daily applications which may be from once a day or less frequently to hourly or more frequently.

The therapeutic activities described were established by state-of-the-art assays. Some examples are as follows using various dilutions of aqueous solutions of 41% by weight of pure sodium N,N-bis-(2-hydroxyethyl)aminoacetate+1.5% by weight sodium hydroxide (total solids=42.5%). For convenience this solution is designated as Solution A.

Example A

Wound Healing Models

1. Incisional model

Two parallel 6 cm incisions were made through the panniculus of rats and a skin separation of at least 1 cm occurred. 200 microliters of Solution A was instilled in the right wound and 200 microliters in the left wound. This procedure was repeated (with different rats) using a 1:5 dilution and a 1:20 dilution of Solution A with pyrogen-free distilled water. The wounds were closed with 6 interrupted 4–0 nylon sutures.

At 7 and 14 days, the animals were sacrificed and 8 mm strips cut from each wound (3 strips per wound, 6 strips per rat). These strips were then disrupted using an Instron 4201 tensiometer and the results expressed as breaking strength in kilograms.

After 14 days, the breaking strength of Solution A was 104% of the control (no solution instillation), the 1:5 dilution of Solution A was 118%, and the 1:20 dilution of Solution A was 198%.

2. Chronic model

Briefly, a chronic, granulating wound was created in a rat by excising a full thickness dorsal scald which had been inoculated with *E. Coli* 5 days after injury. The granulating bed was then treated once with Solution A and, using different rats, with various dilutions (with pyrogen-free distilled water) thereof. Contraction was assessed by serial area measurement of the wound. All areas are expressed as a percentage of the original area and plotted against time. At 7 days a biopsy for quantitative bacteriology was taken to gauge the presence of ongoing infection. At sacrifice the healed wound were disrupted using the tensiometer as previously described.

After 18 days the percent of the wound that was open for Solution A was 53% of the control, a 1:5 dilution of Solution A was 48% of the control, and a 1:20 dilution of Solution A was 77% of the control. Longer periods of observation revealed similar differences.

The antibacterial activities of Solution A and 1:5, 1:10, 1:20 and a 1:40 dilutions of Solution A (with pyrogen-free distilled water) were evaluated versus *E. Coli* ($8 \times 10^7$ organisms), *Ps. aeruginosa* ($6 \times 10^6$ organisms), *S. aureus* ($4 \times 10^5$ organisms), *Strep. pneumoniae* ($4 \times 10^6$ organisms), *S. epidermidis* ($4 \times 10^6$ organisms) and *Strep. faecalis* ($4 \times 10^6$ organisms). Each of these organisms was added to sterile tubes containing 3 ml of the test solution. At times 0, 15, 30 and 60 minutes after addition of the organisms, the solutions were plated (*E. Coli* and *Ps. aeraginosa* on McConkey, all others on blood agar). Colony counts were taken after 24 hours of incubation at 37° C.

The effectiveness of the solutions increased with time. By 60 minutes, Solution A and each of its four dilutions were completely effective in killing *E. Coli and Ps. aeruginosa* whereas only the three higher concentrations completely killed *S. aureus, Strep. pneumoniae, S. epidermidis* and *Strep. faecalis.*

The effect of Solution A and a 1:20, 1:40, 1:60, 1:80, 1:100 and 1:1000 dilutions of Solution A (with pyrogen-free distilled water) on tissue cultured Vero cells was examined. Vero cells were chosen for the propagation and quantitation of herpes simplex viruses and were transformed African green monkey kidney fibroblasts. The medium used in the Vero cell cultures was Earle's minimal essential medium with supplements. Only a very slight detrimental effect on the tissue culture growth was seen with Solution A. However, no detrimental effect was seen with any of the dilutions.

EXAMPLE 1

Preparation of N,N-bis-(2-hydroxyethyl) aminoacetic acid

Methyl bromoacetate (152.98 grams, 1 mole) is dissolved in 1-propanol (500 ml.) and bis-(2-hydroxyethyl)amine (105.14 grams, 2 moles) and triethylamine (111.1 grams, 1.1 moles) are added and the mixture is stirred and heated at reflux for 3 hours. The mixture is treated with 10 normal sodium hydroxide (110 ml., 1.1 moles) and the solvents are removed by distillation in vacuo. The residue is filtered and the solid is washed with 1-propanol. The combined filtrates are dissolved in ethanol (400 ml) and 10 normal sodium hydroxide (130 ml, 1.3 moles) is added. The mixture is stirred and heated at reflux for 3 hours. The mixture is acidified with 12 normal hydrochloric acid (108 ml, 1.3 moles). Upon cooling, N,N-bis-(2-hydroxyethyl)aminoacetic acid separates and is collected by filtration, and is washed with a 50% aqueous ethanol and dried.

EXAMPLE 2

Preparation of sodium N,N-bis-(2-hydroxyethyl)aminoacetate

N,N-Bis-(2-hydroxyethyl)aminoacetic acid (364,933 grams, 2.2144 moles) (this material is 99% pure; it contains 1% or 3.613 grams of $H_2O$) is added with stirring to a cooled solution of pure sodium hydroxide (88.57 grams, 2.2144 moles) in pyrogen-free distilled water (400 ml.). The mixture is stirred until solution is effected. After reaching room temperature, the solution is stirred while enough pyrogen-free distilled water is added to make the total volume 1.000 ml. The solution is sterilized by filtration. This solution is 41% or 2.2144 molar in sodium N,N-bis-(2-hydroxyethyl)aminoacetate.

EXAMPLE 3

Preparation of a combination of sodium N,N-bis-(2-hydroxyethyl)aminoacetate and sodium hydroxide N,N-Bis-(2-hydroxyethyl)aminoacetic acid (364.933 grams, 2.2144 moles) (of 99% material) is added with stirring to a cooled solution of pure sodium hydroxide (103.57 grams, 2.589 moles) in pyrogen-free distilled water. The mixture is stirred until solution is effected. After reaching room temperature, the solution is stirred while enough pyrogen-free distilled water is added to make a total volume of 1,000 ml. The solution is sterilized by filtration. This solution is 41% or 2.2144 molar in sodium N,N-bis-(2-hydroxyethyl)aminoacetate and 1.5% or 0,375 molar in sodium hydroxide. Thus, the solution contains 42.5% of solute. The molar ratio of sodium N,N-bis-(2-hydroxyethyl)aminoacetate to excess hydroxyl ions is 5.9:1. This solution serves as a "stock" solution from which less concentrated solutions can be prepared by diluting 1:5, 1:10, 1:20, 1:50, 1:100, etc. with pyrogen-free sterile distilled water. By using relatively more or less sodium hydroxide as described in Example 3, other combinations are made. One particularly useful molar ratio range of sodium N,N-bis-(2-hydroxyethyl)aminoacetate to excess hydroxyl ions is in the range of 9:1 to 3:1.

EXAMPLE 4

Preparation of other salts of N,N-bis-(2-hydroxyethyl)aminoacetic acid

By carrying out a reaction as described in Example 2 except that the sodium hydroxide is replaced by an equimolar amount of a. lithium hydroxide b. potassium hydroxide c. tetramethylammonium hydroxide d. tetraethylammonium hydroxide e. tetrabutylammonium hydroxide f. benzyltrimethylammonium hydroxide g. guanidine There is obtained, respectively, the a. lithium, b. potassium, c. tetramethylammonium, d. tetraethylammonium, e. tetrabutylammonium, f. benzyltrimethylammonium, g. guanidinium salts of N,N-bis-(2-hydroxyethyl)aminoacetic acid.

EXAMPLE 5

Preparation of combinations of other salts of N,N-bis-(2-hydroxyethyl)aminoacetate and excess base By carrying out a reaction as described in Example 3 except that the sodium hydroxide is replaced by an equimolar amount of the bases listed in Example 4 to give combinations of a. the lithium salt of N,N-bis-(2-hydroxyethyl)aminoacetate and lithium hydroxide, b. the potassium salt of N,N-bis-(2-hydroxyethyl)aminoacetate and potassium hydroxide, c. the tetramethylammonium salt of N,N-bis-(2-hydroxyethyl)aminoacetate and tetramethylammonium hydroxide, d. the tetraethylammonium salt of N,N-bis-(2-hydroxyethyl)aminoacetate and tetraethylammonium hydroxide, e. the tetrabutylammonium salt of N,N-bis-(2-hydroxyethyl)aminoacetate and tetrabutylammonium hydroxide, f. the benzyltrimethylammonium salt of N,N-bis-(2-hydroxyethyl)aminoacetate and benzyltrimethylammonium hydroxide, and g. and the guanidinium salt of N,N-bis-(2-hydroxyethyl)aminoacetate and guanidine.

EXAMPLE 6

Preparation of salts of N,N-bis-(2-hydroxyalkyl)aminoacetates substituted on the 2-carbon atom of the acetate moiety, with and without excess base The procedure as described in Example 1 is repeated eight (8) times except that the bis-(2-hydroxyethyl)amine is replaced by an equimolar amount of one of the following: 1. bis-(2-hydroxypropyl)amine, 2. bis-(2,3-dihydroxypropyl)amine, 3. bis-(1-hydroxy-2-propyl)amine, 4. bis-(2-hydroxy-2-phenylethyl)amine, 5. bis-(1,3-dihydroxy-2-propyl)amine, 6. bis-(3-hydroxypropyl)amine, 7. N-(2-hydroxyethyl)-2-hydroxypropylamine, and 8. N-(2-hydroxyethyl)-3-hydroxypropylamine. The following products are obtained, respectively: 1a. N,N-bis-(2-hydroxypropyl)aminoacetic acid, 2a. N,N-bis-(2,3-dihydroxypropyl)aminoacetic acid, 3a. N,N-bis-(1-hydroxy-2-propyl)aminoacetic acid, 4a. N,N-bis-(2-hydroxy-2-phenylethyl)aminoacetic acid, 5a. N,N-bis-(1,3-dihydroxy-2-propyl)aminoacetic acid, 6a. N,N-bis-(3-hydroxypropyl)aminoacetic acid, 7a. N-(2-hydroxyethyl)-N-(2hydroxypropyl)aminoacetic acid and 8a. N-(2-hydroxyethyl)-N-(3-hydroxypropyl)aminoacetic acid.

The procedure described in Example 2 is repeated eight (8) times except that each time the procedure is repeated the N,N-bis-(2-hydroxyethyl)aminoacetic acid is replaced by one of the eight (8) aminoacetic acids described above. The following products are obtained, respectively: 1b. sodium N,N-bis-(2-hydroxypropyl)aminoacetate, 2b. sodium N,N-bis-(2,3-dihydroxypropyl)aminoacetate, 3b. sodium N,N-bis-(1-hydroxy-2-propyl)aminoacetate, 4b. sodium N,N-bis-(2-hydroxy-2-phenylethyl)aminoacetate, 5b. sodium N,N-bis-(1,3-dihydroxy-2propyl)aminoacetate, 6b. sodium N,N-bis-(3-hydroxypropyl)aminoacetate, 7b. sodium N-(2-hydroxyethyl)-N-(2hydroxypropyl)aminoacetate, and 8b. sodium N-(2-hydroxyethyl)-N-(3-hydroxypropyl)aminoacetate.

The procedure described in Example 3 is repeated eight (8) times except that each time the procedure is repeated the N,N-bis-(2-hydroxyethyl)aminoacetic acid is replaced by an equimolar amount of one of the eight (8) aminoacetic acids described above. The following products are obtained, respectively: 1c. sodium N,N-bis-(2hydroxypropyl)aminoacetate and sodium hydroxide, 2c. sodium N,N-bis-(2,3-dihydroxypropyl)aminoacetate and sodium hydroxide, 3c. sodium N,N-bis-(1-hydroxy-2-propyl)aminoacetate and sodium hydroxide, 4c. sodium N,N-bis-(2-hydroxy-2-phenylethyl)aminoacetate and sodium hydroxide, 5c. sodium N,N-bis-(1,3-dihydroxy-2-propyl)aminoacetate and sodium hydroxide, 6c. sodium N,N-bis-(3hydroxypropyl)aminoacetate and sodium hydroxide, 7c. sodium-N-(2-hydroxyethyl)-N-(2-hydroxypropyl)aminoacetate and sodium hydroxide, and 8c. sodium N-(2-hydroxyethyl)-N-(3-hydroxypropyl)aminoacetate and sodium hydroxide.

The procedure described in Example 4 is repeated eight (8) times except that each time the procedure is repeated the N,N-bis-(2-hydroxyethyl)aminoacetic acid is replaced by one of the eight (8) aminoacetic acids described above. The following products are obtained, respectively: the (1) lithium, (2) potassium, (3) tetramethylammonium, (4) tetraethylammonium, (5) tetrabutylammonium, (6) benzyltrimethylammonium, and (7) guanidinium salts of each of one of these aminoacetic acids.

The procedure described in Example 5 is repeated eight (8) times except that each time the procedure is repeated the N,N-(bis-2-hydroxyethyl)aminoacetic acid is replaced by an equimolar amount of one of the eight (8) aminoacetic acids described above. Combinations of one of the seven (7) salts of each of the eight (8) aminoacetic acids plus the base used to form the salt are obtained.

EXAMPLE 7

Preparation of sails of
N,N-bis-(2-hydroxyethyl)aminoacetate substituted
on the 2-carbon atom of the acetate moiety By following the procedure described in Example 1, except that the methyl bromoacetate is replaced by an equimolar amount of:
a. methyl 2-bromopropanoate,
b. methyl 2-bromosuccinamate,
c. methyl 2-bromo-3-phenylpropanoate,
d. methyl 2-bromoisovalerate,
e. methyl 2-bromohydracrylate,
f. methyl 2-bromo-2-(3-pyridyl)acetate,
g. The L-enantiomer of methyl 2-bromopropanoate,
h. The D-enantiomer of methyl 2-bromopropanoate
i. Methyl 2-bromo-3,3,3-trifluoropropanoate and
j. Methyl 2-bromo 2 phenylacetate,
there is obtained, respectively,
a-1. 2-[N,N-bis-(2-hydroxyethyl)amino]propanoic acid,
b-1. 2-[N,N-bis-(2-hydroxyethyl)amino]succinamic acid,
c-1. 2-[N,N-bis-(2-hydroxyethyl amino]-4-phenylbutanoic acid,
d-1. 2-[N,N-bis-(2-hydroxyethyl)amino]isovaleric acid,
e-1. 2-[N,N-bis-(2-hydroxyethyl)amino]hydracrylic acid,
f-1. [N,N-bis-(2-hydroxyethyl)amino]-(3-pyridyl)acetic acid,
g-1. The L-enantiomer of 2-[N,N-bis-(2-hydroxyethyl)amino]propanoic acid,
h-1. The D-enantiomer of 2-[N,N-bis-(2-hydroxyethyl)amino] propanoic acid,
i-1. 2-[N,N-bis-(2-hydroxyethyl)amino]-3,3,3-trifluoropropanoic acid and
j-1. [N,N-bis-(2-hydroxyethyl)amino]phenylacetic acid.

By following the procedure described in Example 2, except that the N,N-bis-(2-hydroxyethyl)aminoacetic: acid is replaced by the ten (10) acetic acids noted above, there is obtained, respectively,
a-2. sodium 2-[N,N-bis-(2-hydroxyethyl)amino]propanoate,
b-2 sodium 2-[N,N-bis-(2-hydroxyethyl)amino]succinamate,
c-2. sodium 2-[N,N-bis-(2-hydroxyethyl)amino]-4-phenylbutanoate,
d-2 sodium 2-[N,N-bis-(2-hydroxyethyl)amino]isovalerate,
e-2. sodium 2-[N,N-bis-(2-hydroxyethyl)amino]hydracrylate,
f-2 sodium 2-[N,N-bis-(2-hydroxyethyl)amino]-(3-pyridyl)acetate,
g-2 The L-enantiomer of sodium 2-[N,N-bis-(2-hydroxyethyl)amino]propanoate,
h-2. The D-enantiomer of sodium 2-[N,N-bis-(2-hydroxyethyl)amino]propanoate,
i-2. sodium 2-[N,N-bis-(2-hydroxyethyl)amino]-3,3,3-trifluoropropanoate and
j-2. sodium [N,N-bis-(2-hydroxyethyl)amino] phenylacetate
By following the procedure described except that the N,N-bis-(2-hydroxyethyl)aminoacetic acid is replaced by an equimolar amount of the ten (10) acetic acids noted above, there is obtained, respectively,
a-3. sodium 2-[N,N-bis-(2-hydroxyethyl)amino]propanoate and sodium hydroxide,
b-3. sodium 2-[N,N-bis-(2-hydroxyethyl)amino]succinamate and sodium hydroxide,
c-3. sodium 2-[N,N-bis-(2-hydroxyethyl)amino]-4-phenylbutanoate and sodium hydroxide,
d-3. sodium 2-[N,N-bis-(2-hydroxyethyl)amino]-isovalerate and sodium hydroxide,
e-3. sodium 2-[N,N-bis-(2-hydroxyethyl)amino]hydracrylate and sodium hydroxide,
f-3. sodium 2-[N,N-bis-(2-hydroxyethyl)amino]-(3pyridyl)acetate and sodium hydroxide,
g-3. The L-enantiomer of sodium 2-[N,N-bis-(2-hydroxyethyl)amino]propanoate and sodium hydroxide,
h-3. The D-enantiomer of sodium 2-[N,N-bis-(2-hydroxyethyl) amino]propanoate and sodium hydroxide,
i-3. sodium 2-[N,N-bis-(2-hydroxyethyl)amino]-3,3,3-trifluoropropanoate and sodium hydroxide and j-3. sodium [N,N-bis-(2-hydroxyethyl)amino]phenylacetate and sodium hydroxide.

By following the procedure described in Example 4, except that the N,N-bis-(2-hydroxyethyl)aminoacetic acid is replaced by an equimolar amount of the ten (10) substituted acetic acids noted above, there is obtained, respectively the (1) lithium, (2) potassium, (3) tetramethylammonium, (4) tetraethylammonium, (5) tetrabutylammonium, (6) benzyltrimethylammonium and (7) guanidinium salts of each of these ten (10) acetic acids.

By following the procedure described in Example 5, except the N,N-bis-(2-hydroxyethyl)aminoacetic acid is replaced by an equimolar amount of the ten (10) acetic acids noted above, there is obtained, respectively, the (1) lithium, (2) potassium, (3) tetramethylammonium, (4) tetraethylammonium, (5) tetrabutylammonium, (6) benzylmethylammonium, and (7) guanidinium salts of each of these ten (10) acetic acids, each with a molar ratio of substituted acetate salt to excess base of 9:1 to 3:1 by using the same base that was used to prepare the salt.

EXAMPLE 8

Preparation of salts of
2-[N,N-bis-(2,3-dihydroxypropyl)amino]isovalerate
with and without excess base By conducting the procedure described in Example 1, except that the bis-(2-hydroxyethyl)amine is replaced by an equimolar quantity of bis-(2,3-dihydroxypropyl)amine and the methyl bromoacetate is replaced by an equimolar quantity of methyl 2-bromoisovalerate, there is obtained 2-[N,N-bis-(2,3-dihydroxypropyl)amino]isovaleric acid.

By carrying out the procedure described in Example 2 except that the N,N-bis-(2-hydroxyethyl)aminoacetic acid is replaced by an equimolar quantity of 2-[N,N-bis-(2,3-dihydroxypropyl)amino] isovaleric acid, there is obtained sodium 2-[N,N-bis-(2,3-dihydroxypropyl)amino]isovalerate.

By carrying out the procedure described in Example 3 except that the N,N-bis-(2-hydroxyethyl)aminoacetic acid is replaced by an equimolar quantity of 2-[N,N-bis-(2,3-dihydroxypropyl)amino] isovaleric acid, there is obtained a mixture of 2.214 molar sodium 2-[N,N-bis-(2,3-dihydroxypropyl)amino]isovalerate and 0.375 molar sodium hydroxide.

By carrying out the procedure described in Example 4 except that the N,N-bis-(2-hydroxyethyl)aminoacetic acid is replaced by an equimolar quantity of 2-[N,N-bis-(2,3-dihydroxypropyl)amino]isovaleric acid, there is obtained the lithium, potassium, tetramethylammonium, tetraethylammonium, tetrabutylammonium, benzyltrimethylammonium and guanidinium salts of 2-[N,N-bis-(2,3-dihydroxypropyl)amino]isovaleric acid.

By carrying out the procedure described in Example 5 except that the N,N-bis-(2-hydroxyethyl)aminoacetic acid is replaced by an equimolar amount of 2-[N,N-bis-(2,3-dihydroxypropyl)amino] isovaleric acid, there is obtained lithium 2-[N,N-bis-(2,3-dihydroxypropyl)amino]isovalerate and lithium hydroxide, potassium 2-[N,N-bis-(2,3-dihydroxypropyl)amino] isovalerate and potassium hydroxide, tetramethylammonium 2-[N,N-bis-(2,3-dihydroxypropyl)amino] isovalerate and tetramethylammonium hydroxide, tetraethylammonium 2-[N,N-bis-(2,3-dihydroxypropyl)amino] isovalerate and tetraethylammonium hydroxide, tetrabutylammonium 2-[N,N-bis-(2,3-dihydroxypropyl)amino] isovalerate and tetrabutylammonium hydroxide, benzyltrimethylammonium 2-[N,N-bis-(2,3-dihydroxypropyl)amino] isovalerate and benzyltrimethylammonium hydroxide, and guanidinium 2-[N,N-bis-(2,3-dihydroxypropyl)amino] isovalerate and guanidine.

EXAMPLE 9

Preparation of a solution of sodium
N,N-bis-(2-hydroxy-ethyl)aminoacetate plus sodium
hydroxide for topical administration One hundred ml. of a solution 2.2144 molar in N,N-bis-(2-hydroxyethyl)aminoacetate and 0.375 molar in sodium hydroxide in pyrogen-free distilled water is diluted to 1000 ml. using sterile pyrogen-free water and sterile vessels. The resulting solution is used for applying to tissue surfaces by painting, using a sterile cotton swab, spraying from a bottle or from an atomizer.

In a similar way other molar ratios of sodium N,N-bis-(2-hydroxyethyl)aminoacetate to sodium hydroxide may be used, as well as other concentrations of total solids. Likewise, the other salts of N,N-bis-(2-hydroxyethyl)aminoacetate listed in Example 4 and the other bases listed in Example 5 may be used instead of those listed above. In addition, the other modulating salts and bases listed in Examples 6, 7 and 8 may be substituted for the sodium N,N-bis-(2-hydroxyethyl)aminoacetate and sodium hydroxide.

EXAMPLE 10

Preparation of a solution of sodium
N,N-bis(2-hydroxyethyl)aminoacetate plus sodium
hydroxide for topical administration Fifty ml. of a solution 2.2144 molar in sodium N,N-bis-(2-hydroxyethyl)aminoacetate and 0.375 molar in sodium hydroxide in pyrogen-free distilled water plus 50 ml. of a solution 2. 2144 molar in sodium N,N-bis-(2-hydroxypropyl)aminoacetate and 0.375 molar in sodium hydroxide in pyrogen-free distilled water is diluted to 1000 ml. using sterile pyrogen-free water and sterile vessels. This solution is used for applying to tissue surfaces by painting, using a sterile cotton swab, spraying from a bottle or from an atomizer.

In a similar way other molar ratios of sodium N,N-bis-(2-hydroxyethyl)aminoacetate plus sodium N,N-bis-(2-hydroxypropyl)aminoacetate to sodium hydroxide may be used, as well as other concentrations of total solids. Likewise, the other salts of N,N-bis-(2-hydroxyethyl)aminoacetate listed in Example 4 and of N,N-bis-(2-hydroxypropyl)aminoacetate listed in Example 6 and the other bases listed in Examples 5, 6 and 7 may be used instead of those listed above. In addition, mixtures of the other modulating salts and bases listed in Examples 3, 4, 5, 6, 7 and 8 may be used instead of sodium N,N-bis-(2-hydroxyethyl)aminoacetate, sodium N,N-bis-(2-hydroxypropyl)aminoacetate and sodium hydroxide as described above.

EXAMPLE 11

Preparation of a solid mixture of sodium
N,N-bis-(2-hydroxyethyl)aminoacetate and sodium
hydroxide One hundred ml. of a solution 2.2144 molar in sodium N,N-bis-(2-hydroxyethyl)aminoacetate and 0.0375 molar in sodium hydroxide in pyrogen-free distilled water was lyophilized (freeze dried) to give a solid residue. This solid is used to regenerate a solution of any desired concentration by adding pyrogen-free sterile distilled water. It also can be pulverized under sterile conditions and placed in a standard aerosol dispenser for administration to tissue surfaces by aerosol.

In a similar way other molar ratios of sodium N,N-bis-(2-hydroxyethyl)aminoacetate to sodium hydroxide may be used, as well as other concentrations of total solids. Likewise, the other salts of N,N-bis-(2-hydroxyethyl) aminoacetic acid listed in Example 4 and the other bases listed in Example 5 may be used instead of those listed above. In addition, the other modulating salts and bases listed in Examples 6, 7 and 8 may be substituted for the sodium N,N-bis-(2-hydroxyethyl) aminoacetate and sodium hydroxide.

EXAMPLE 12

Preparation of ointments and creams containing sodium N,N-bis-(2-hydroxyethyl)aminoacetate and sodium hydroxide The solid residue of sodium N,N-bis-(2-hydroxyethyl)aminoacetate and sodium hydroxide obtained in Example 11 by lyophilization is pulverized under sterile conditions and mixed into standard ointments and creams so that the total concentration of sodium N,N-bis-(2-hydroxyethyl)aminoacetate plus sodium hydroxide is in the range of 1% to 15% of the total mixture. These ointments and creams are applied to the tissues for wound healing therapy.

In a similar way other molar ratios of sodium N,N-bis-(2-hydroxyethyl)aminoacetate to sodium hydroxide may be used, as well as other concentrations of total solids. Likewise, the other salts of N,N-bis-(2-hydroxyethyl)aminoacetic acid listed in Example 4 and the other bases listed in Example 5 may be used instead of those listed above. In addition, the other modulating salts and bases listed in Examples 6, 7 and 8 may be substituted for the sodium N,N-bis-(2-hydroxyethyl)aminoacetate and sodium hydroxide.

While this invention has been described with respect to various specific examples and embodiments, it is to be understood that the invention is not limited thereto and that it can be variously practiced within the scope of the following claims.

What is claimed is:

1. A hydroxyl ion modulating compound having the formula

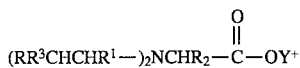

wherein each R is independently selected from the group consisting of H, alkyl, hydroxyalkyl, cycloalkyl, aryl and substituted counterparts thereof; each $R^1$ is independently selected from the group consisting of H, alkyl, hydroxyalkyl and substituted counterparts thereof; $R^2$ is selected from the group consisting of H, alkyl, cycloalkyl, aryl, aralkyl, heterocyclic including at least one heteroatom selected from the group consisting of N, S and O, hetercyclicalkyl including at least one heteroatom selected from the group consisting of N, S and O, and substituted counterparts thereof, provided that when $R^2$ is H, n-alkyl, $CH_2OH$ or phenylalkyl, one or both $RR^3CHCHR^1$— groups are other than $CH_2$ or $CH_3CHOHCH_2$—; each $R^3$ is independently selected from the group consisting of H, alkyl, hydroxyalkyl, hydroxy, aryl and substituted counterparts thereof, provided that at least one R is hydroxyalkyl or at least one $R^3$ is hydroxy or hydroxyalkyl; and $Y^+$ is selected from the group consisting of $Na^+$, $K^+$, $Li^+$, $(CH_3)_4N^+$, $(C_2H_5)_4N^+$, $C_6H_5(CH_3)_3N^+$, guanidinium.

2. The hydroxyl ion modulating compound of claim 1 wherein each R is independently selected from the group consisting of H, alkyl having 1 to 4 carbon atoms, phenyl and hydroxyalkyl having 1 to 4 carbon atoms; each $R^1$ is independently selected from the group consisting of H, alkyl having 1 to 3 carbon atoms and hydroxyalkyl having 1 to 3 carbon atoms; $R^2$ is selected from the group consisting of alkyl having 1 to 5 carbon atoms, hydroxyalkyl having 1 to 5 carbon atoms, phenyl, phenylalkyl, heterocyclic, heterocyclicalkyl and cycloalkyl having 3 to 6 carbon atoms; and each $R^2$ is independently selected from the group consisting of H, alkyl, hydroxyalkyl, hydroxy and phenyl.

3. The hydroxyl ion modulating compound of claim 1 wherein R is selected from the group consisting of H, $CH_3$, $CH_2OH$ and $C_6H_5$; $R^2$ is selected from the group consisting of H, $CH_3$, $CH_2OH$ and $C_2H_5$; and $R^2$ is selected from the group consisting of $(CH_3)_2CH$—, $NH_2COCH_2$—, $C_6H_5$—, cyclopentyl,

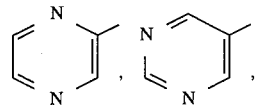

$CF_3$ and $CH_3CH_3CH(CH_3)$—; and $R^3$ is selected from the group consisting of H, OH, $CH_3$ and $C_2H_5$.

4. The hydroxyl ion modulating compound of claim 2 wherein R is selected from the group consisting of $CH_3$, $CH_2OH$ and $C_6H_5$; $R^1$ is selected from the group consisting of H, $CH_3$ and $CH_2OH$; $R^2$ is selected from the group consisting of $NH_2COCH_2$—, $C_6H_5$—, $(CH_3)_2CH$—,

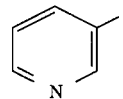

and $CF_3$; and $R^3$ is selected from the group consisting of H and OH.

5. The hydroxyl ion modulating compound of claim 1 selected from the group consisting of sodium salts of an acid, potassium salts of an acid, tetramethylammonium salts of an acid, tetraethylammonium salts of an acid, benzyltrimethylammonium salts of an acid and guanidinum salt of an acid; said acids being selected from the group consisting of N,N-bis-(2,3-dihydroxypropyl) aminoacetic acid, N,N-bis-(1-hydroxy-2-propyl)aminoacetic acid, N,N-bis-(2-hydroxy-2-phenylethyl)aminoacetic acid 2-[N,N-bis-(2-hydroxyethyl)amino]succinamic acid, 2- [N,N-bis-(2-hydroxyethyl)amino]-4-phenyl butanoic acid, 2-[N,N-bis-(2-hydroxyethyl)amino]isovaleric acid, 2-N,N[N,N=bis-(2-hydroxyethyl)amino]-(3pyridyl)acetic acid, 2-[N,N-bis-(2-hydroxyethyl)amino]-3,3,3-trifluoropropanoic acid, [N,N-bis-(2-hydroxyethyl)amino]phenylacetic acid, N,N-[bis-(1,3-dihydroxy-2-propyl)amino]acetic acid, 2-[N,N-bis-(2,3-dihydroxypropyl)amino]isovaleric acid, N-N-bis (3-hydroxypropyl)aminoacetic acid, N-(2hydroxyethyl)-N-(2-hydroxypropyl)aminoacetic acid and N(2-hydroxyethyl)-N-(3-hydroxypropyl)aminoacetic acid.

6. The hydroxyl ion modulating compound of claim 1 wherein $Y^+$ is selected from the group consisting of $Na^+$, $K^+$ and $Li^+$.

7. The hydroxyl ion modulating compound of claim 1 wherein $Y^+$ is selected from the group consisting of $Na^+$, $K^+$, $(CH_3)_4N^+$, $(C_2H_5)_4$, $N^+$, $C_6H_5(CH_3)N^+$ and guanidinium.

8. The hydroxyl ion modulating compound of claim 1 wherein $Y^+$ is selected from the group consisting of $Na^+$ and $K^+$.

9. The hydroxyl ion modulating compound of claim 1 wherein $Y^+$ is $Na^+$.

10. The hydroxyl ion modulating compound of claim 1 selected from the group consisting of:
sodium N,N-bis-(2,3-dihydroxypropyl)aminoacetate,
sodium N,N-bis -(1-hydroxy-2-propyl)aminoacetate,
sodium N,N-bis -(2-hydroxy- 2-phenylethyl)aminoacetate,
sodium N,N-[bis -(2-hydroxyethyl)amino]isovalerate,
sodium N,N-[bis-(2- hydroxyethyl)amino ]phenylacetate,
sodium 2-N,N-[N,N-bis-(2-hydroxyethyl)amino]-(3-pyridyl)acetate,
sodium N,N-[bis-(1,3-dihydroxy-2-propyl)amino]acetate,
sodium N,N-bis-(3-hydroxypropyl)aminoacetate,
sodium N-(2-hydroxyethyl)-N-(2-hydroxypropyl)aminoacetate, and
sodium N-(2-hydroxyethyl)-N-(3-hydroxypropyl)aminoacetate.

* * * * *